US00PP23577P2

(12) United States Plant Patent
Giesen

(10) Patent No.: US PP23,577 P2
(45) Date of Patent: Apr. 30, 2013

(54) *LOBELIA* PLANT NAMED 'LOBZ0002'

(50) Latin Name: *Lobelia erinus*
Varietal Denomination: LOBZ0002

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 69 days.

(21) Appl. No.: 13/317,194

(22) Filed: Oct. 12, 2011

(51) Int. Cl.
*A01H 5/00* (2006.01)

(52) U.S. Cl. ..... Plt./451

(58) Field of Classification Search ..... Plt./451
See application file for complete search history.

*Primary Examiner* — Kent L Bell
(74) *Attorney, Agent, or Firm* — Joshua L. Price

(57) ABSTRACT

A new *Lobelia* plant named 'LOBZ0002' particularly distinguished by has large pure white flowers, long inflorescences with good floriferousness, medium green foliage, narrow leaves, freely branching and tight relatively upright plant habit, and relatively strong vigor.

1 Drawing Sheet

Latin name of the genus and species of the plant claimed: *Lobelia erinus.*

Varietal denomination: 'LOBZ0002'.

BACKGROUND OF THE NEW PLANT

The present invention comprises a new and distinct cultivar of *Lobelia*, botanically known as *Lobelia erinus* and hereinafter referred to by the cultivar name 'LOBZ0002'.

'LOBZ0002' is a product of a planned breeding program. The new cultivar has large pure white flowers, long inflorescences with good floriferousness, medium green foliage, narrow leaves, freely branching and tight relatively upright plant habit, and relatively strong vigor.

'LOBZ0002' originated from a hybridization made in February 2007 in Andijk, Netherlands.

The female parent was the unpatented, proprietary plant designated 'LOB07-244-2', having smaller flowers, with shorter and lighter green foliage.

The male parent of 'LOBZ0002' was the proprietary, unpatented plant designated 'LOB07-223-1', having a less upright plant habit, bigger flowers and thinner stems. The resulting seeds were sown in May 2007.

'LOBZ0002' was selected as one flowering plant within the progeny of the stated cross in July 2007 in a controlled environment in Andijk, Netherlands.

The first act of asexual reproduction of 'LOBZ0002' was accomplished when vegetative cuttings were propagated from the initial selection in the late summer of 2007 in a controlled environment in Andijk, Netherlands.

BRIEF SUMMARY OF THE INVENTION

Horticultural examination of plants grown from cuttings of the plant initiated in the spring of 2008 in Andijk, Netherlands, and continuing thereafter, has demonstrated that the combination of characteristics as herein disclosed for 'LOBZ0002' are firmly fixed and are retained through successive generations of asexual reproduction.

'LOBZ0002' has not been observed under all possible environmental conditions. The phenotype may vary significantly with variations in environment such as temperature, light intensity and day length.

A Plant Breeder's Right for this cultivar was applied for in Canada on Dec. 24, 2010, #10-7139. 'LOBZ0002' has not been made publicly available more than one year prior to the filing of this application.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

The accompanying photographic drawing shows typical flower and foliage characteristics of 'LOBZ0002' with colors being as true as possible with an illustration of this type. The photographic drawing shows a flowering plant of the new variety and a close-up of its flowers.

DETAILED BOTANICAL DESCRIPTION

The aforementioned photographs were taken in May 2011 of plants grown in a greenhouse trial in Andijk, Netherlands. These plants were grown in 10.5 cm pots and were approximately 14 weeks of age.

The measurements were taken in Andijk, Netherlands in mid May 2011 on 13 week old plants that were growing in 10.5 cm pots in a greenhouse at relatively cool conditions. Plants received 1 terminal pinch of the apices at an early age. Color chart used: The Royal Horticultural Society Colour Chart (R.H.S.), 2001.

TABLE 1

DIFERENCE BETWEEN THE NEW VARIETY 'LOBZ0002' AND SIMILAR VARIETIES

| | 'LOBZ0002' | 'Weslowhite' (U.S. Plant Pat. No. 16,295) | 'Tec Hewhitt' (U.S. Plant Pat. No. 21,988) |
|---|---|---|---|
| Flower color: | Pure white | White with light purple spots on petals, and very pale purple tube | Pure white |

TABLE 1-continued

DIFERENCE BETWEEN THE NEW VARIETY 'LOBZ0002' AND SIMILAR VARIETIES

| | 'LOBZ0002' | 'Weslowhite' (U.S. Plant Pat. No. 16,295) | 'Tec Hewhitt' (U.S. Plant Pat. No. 21,988) |
|---|---|---|---|
| Flower, diameter: | 2.7 cm | 1.8 cm | 2.7 cm |
| Pubescence on leaf and stem: | Present moderately dense | Present/strong | Absent/glabrous leaves and nearly glabrous stems |
| Plant habit: | Upright | More trailing/ cascading | Vigorously trailing |

Plant:

*Growth and habit*.—Vigorous growth habit; dense and freely branched, short internodes, and nice mounding habit.

*Height*.—About 8.0 cm (from top of soil).

*Height* (*inflorescence included*).—About 12.0 cm.

*Width* (*horizontal diameter*).—22.0 cm.

*Time to initiate and develop roots*.—21-28 days at 68° F.-74° F. (20-23° Centigrade).

*Root description*.—Fibrous and freely branching.

Foliage:

*Arrangement*.—Alternate, sessile.

*Immature leaf, color upper surface*.—RHS 137D.

*Immature leaf, color lower surface*.—RHS 146B.

*Mature color upper surface*.—Between RHS 137B and RHS137C.

*Mature color lower surface*.—RHS 147B.

*Leaf length*.—3.5-7.0 cm.

*Leaf width*.—0.5-2.0 cm.

*Shape*.—Oblanceolate to elliptic low on the plant and narrower, oblanceolate leaves higher on the plant.

*Apex*.—Obtuse.

*Base*.—Attenuate.

*Margin*.—Entire to slightly incised.

*Venation type*.—Pinnate.

*Venation color, upper surface*.—RHS 143C.

*Venation color, lower surface*.—RHS 143C.

*Texture*.—Pubescent on both surfaces.

Stem:

*Color*.—RHS 137A; 143B on younger stems.

*Quantity of main branches per plant*.—6 main stems, each with 3 to 4 secondary branches.

*Stem length*.—3.0-6.0 cm.

*Diameter*.—0.5 cm.

*Internode length*.—1.5 cm.

*Texture*.—Pubescent.

Peduncle:

*Color*.—RHS 137B.

*Length*.—14.0-18.5 cm.

*Diameter*.—0.3 cm.

*Texture*.—Pubescent.

Pedicels:

*Color*.—RHS 137B.

*Length*.—2.0 cm.

*Diameter*.—0.1 cm.

*Texture*.—Pubescent.

Inflorescence:

*Type of inflorescence*.—Raceme, composed of single flowers in an alternate arrangement with one flower per node, subtended by a small leaflet.

*Blooming habit*.—Continuous through the growing season from spring to the fall.

*Quantity of inflorescences per plant*.—About 75.

*Quantity of flowers per inflorescence*.—About 17 open flowers and additional buds.

*Lastingness of individual blooms on the plant*.—3-6 days, depending on temperature.

*Fragrance*.—None.

*Inflorescence length*.—10.0-17.0 cm.

Flower:

*Corolla type and shape*.—Single, zygomorphic; upper lip is formed by two small petals, lower lip has three larger petals; petals are fused at the base forming a relatively long funnel-shaped tube.

Immature flower:

*Main color upper surface*.—RHS 150D.

*Main color lower surface*.—RHS 150D.

*Immature flower, width*.—1.7 cm.

Mature flower:

*Flower*, (*horizontal*) *length*.—2.7 cm.

*Flower*, (*horizontal*) *width*.—2.5 cm.

*Flower, vertical length* (*depth*).—1.4 cm.

*Color upper lip, upper surface*.—RHS 155D but Whiter.

*Color upper lip, lower surface*.—RHS 155D but whiter.

*Upper petal lobes, length* (*from the tube opening*).—0.4 cm.

*Upper petal lobes, width*.—0.2 cm.

*Color lower lip, upper surface*.—RHS 155D but whiter.

*Color lower lip, lower surface*.—RHS 155D but whiter.

*Nectaries at base of lower petals*.—RHS N144D.

*Lower petal lobes, length* (*from the corolla opening*).—0.8 cm.

*Lower petal lobes, width*.—0.4-0.6 cm.

*Tube, color* (*outside*).—RHS 155C or 157D.

*Tube length*.—0.9 cm.

*Tube width*.—0.4 cm.

Petal (lobes):

*Shape*.—Obovate.

*Apex*.—Mucronulate.

*Base*.—Fused.

*Margin*.—Entire.

*Texture upper surface*.—Glabrous.

*Texture lower surface*.—Short hair, mainly along the mid vein.

Flower bud:

*Shape*.—Elongate.

*Length*.—1.4 cm.

*Diameter*.—0.5 cm.

*Color* (*at tight bud*).—Between RHS 150C and 150D.

Calyx:

*Shape*.—5 sepals in a whorl, slanting outwards with bases fused.

*Sepal color*.—RHS 137C.

*Sepal length* (*fee ends*).—1.1 cm.

*Sepal width*.—0.2 cm for the funnel shaped part.

*Shape*.—Ligulate.

*Apex*.—Acute.

*Base*.—Fused.

*Texture*.—Pubescent.

Reproductive organs:

Stamens:

*Quantity.*—5.

*Filament, color.*—RHS 154A.

*Filament length.*—0.4 cm.

*Filament, diameter.*—0.1 cm.

*Anther color.*—RHS 154A.

*Anther length.*—0.2 cm.

*Pollen amount.*—None.

*Pollen color.*—None.

Pistil:

*Quantity per flower.*—1.

*Length.*—About 1.0 cm.

*Stigma color.*—RHS 198A.

*Stigma length.*—0.25 cm.

*Style color.*—RHS 155D.

*Style length.*—0.6-0.8 cm.

Fruit and seed set: Fruit and seed set have not been observed on this hybrid.

Disease and insect resistance: Disease/pest resistance has not been observed on this hybrid.

It is claimed:

1. A new and distinct cultivar of *Lobelia* plant named 'LOBZ0002' substantially as illustrated and described herein.

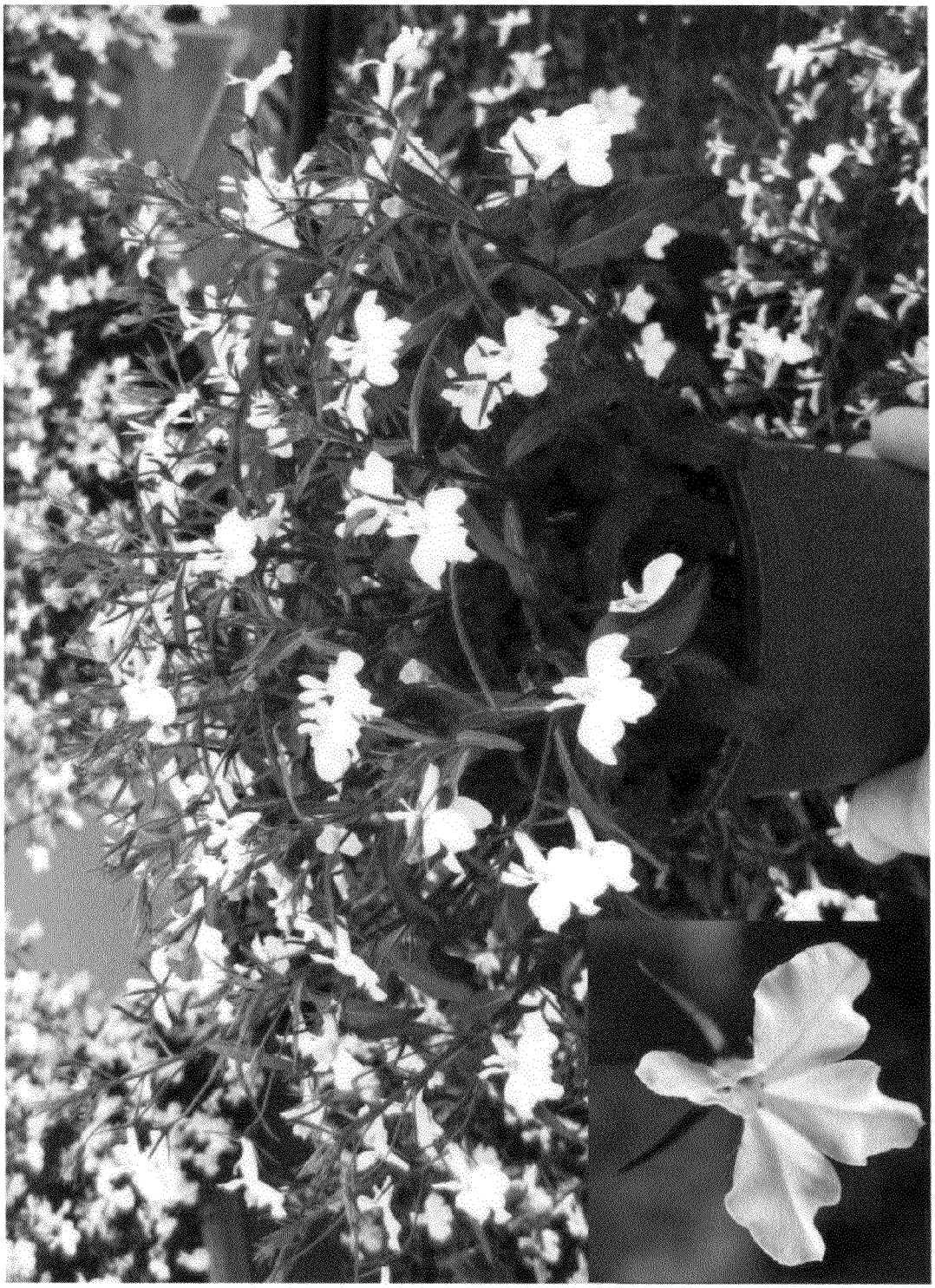

* * * * *